United States Patent [19]

Newton

[11] 4,175,544
[45] Nov. 27, 1979

[54] IODO-ARYL CARBONATES FOR USE IN METHODS IN RADIOGRAPHY

[75] Inventor: Barry N. Newton, Lafayette, Ind.

[73] Assignee: Lafayette Pharmacal Inc., Lafayette, Ind.

[21] Appl. No.: 920,114

[22] Filed: Jun. 28, 1978

Related U.S. Application Data

[60] Continuation-in-part of Ser. No. 766,062, Feb. 7, 1977, abandoned, which is a division of Ser. No. 679,393, Apr. 22, 1976, Pat. No. 4,022,814, which is a continuation-in-part of Ser. No. 501,169, Aug. 28, 1974, abandoned.

[51] Int. Cl.² .......................... A61B 5/00; A61K 29/02
[52] U.S. Cl. ........................................... 128/654; 424/5
[58] Field of Search ........................... 424/5; 128/2 R

[56] References Cited

U.S. PATENT DOCUMENTS

| | | | |
|---|---|---|---|
| 2,348,231 | 5/1944 | Strain et al. | 424/5 X |
| 2,386,640 | 10/1945 | Strain et al. | 424/5 X |
| 3,178,473 | 4/1965 | Holtermann et al. | 424/5 X |
| 3,235,461 | 2/1966 | Habicht et al. | 424/5 |
| 3,676,486 | 7/1972 | Nikles | 260/463 |
| 3,883,578 | 5/1975 | Gries | 424/5 X |

*Primary Examiner*—James O. Thomas, Jr.
*Assistant Examiner*—Vera C. Clarke

*Attorney, Agent, or Firm*—Woodard, Weikart, Emhardt & Naughton

[57] ABSTRACT

A method for using iodo-aryl carbonates, such as for example, p-iodo-benzyl carbonates, p-iodo-sec-phenethyl carbonates, p-iodo-phenethyl carbonates, p-iodo-phenyl carbonates, 3-(p-iodophenyl)propyl carbonates, 3-(p-iodophenyl)butyl carbonates, 2-(p-iodobenzyl)butyl carbonates and 2-(p-iodobenzyl)-n-hexyl carbonates, to provide radiopaques for various radiography purposes in connection with such techniques as X-ray applications including myelography, salpingography, lymphography and bronchography. The method first comprises selecting a compound generally categorized as a carbonate and having the general formula

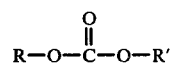

wherein R represents an alkyl group having from 1 to 10 carbon atoms and R' represents an iodinated phenyl linked directly to the ester oxygen or through an alkyl chain consisting of 1 to 3 carbon atoms. An effective amount of a pharmaceutically acceptable carbonate, as defined herein, is then placed into the subject body cavity and the particular X-ray or other study performed of this area.

9 Claims, No Drawings

IODO-ARYL CARBONATES FOR USE IN METHODS IN RADIOGRAPHY

RELATED APPLICATIONS

This application is a continuation-in-part of a copending U.S. patent application, Ser. No. 766,062, filed Feb. 7, 1977 and entitled "Method for Providing a Radiopaque for Radiography Purposes." U.S. patent application, Ser. No. 766,062, now abandoned is a division of U.S. patent application, Ser. No. 679,393, filed Apr. 22, 1976 and entitled "Iodine Containing Organic Carbonates for Use as Radiographic Agents," which has since issued as U.S. Pat. No. 4,022,814. U.S. patent application, Ser. No. 679,393 was, in turn, a continuation-in-part of now-abandoned U.S. patent application, Ser. No. 501,169, filed Aug. 28, 1974 and entitled "Iodine Containing Organic Carbonates for Use as Radiographic Agents."

BACKGROUND OF THE INVENTION

The present invention relates to contrast media for radiography, and more particularly to the preparation and use of iodinated organic carbonates as contrast media for radiography. More specifically, the present invention relates to the preparation and use as radiographic media of iodinated benzyl carbonates, p-iodo-sec-phenethyl carbonates (sec means secondary or two groups attached to the same carbon atom of the ethyl moiety), p-iodo-phenethyl carbonates, p-iodo-phenyl carbonates, 3-(p-iodophenyl)propyl carbonates, 3-(p-iodophenyl)butyl carbonates, 2-(p-iodobenzyl)butyl carbonates and 2-(p-iodobenzyl)-n-hexyl carbonates.

Myelography and possibly other X-ray applications for body cavities have been performed with iodinated oils. Such radiographic agents after being introduced into the subarachnoid space or other body cavities must be withdrawn because of their incomplete absorption even after periods of several years. Other areas of radiography, lymphography and bronchography utilize contrast media which have proven to be irritating and slowly eliminated, and to produce undesirable side effects in addition to being difficult to administer.

Illustrative prior art methods and compositions for radiography are disclosed in U.S. Pat. No. 3,178,473 issued Apr. 13, 1965 to H. Haltermann et al. for "Process for the N-alkylation of Acyl Anilides Halogen Substituted in the Nucleus"; U.S. Pat. No. 2,386,640 issued Oct. 9, 1945 to W. H. Strain et al. for "Bis Esters of Iodinated Phenyl Aliphatic Carboxylic Acids"; U.S. Pat. No. 3,235,461 issued Feb. 15, 1966 to E. Habicht et al. for "Esters of 3,5-Diiodo-4-Pyridone-N-Acetic Acid"; and U.S. Pat. No. 2,348,231 issued May 9, 1944 to W. H. Strain et al. for "Compounds for Use in Radiography."

SUMMARY OF THE INVENTION

One embodiment of the present invention comprises a method for visualizing an inner body cavity including the steps of first selecting a pharmaceutically acceptable iodinated phenyl carbonate compound, placing an amount of the compound into a body cavity and then X-raying the cavity.

This embodiment constitutes a significant improvement over prior art methods employing various other radiographic agents as previously discussed herein. The use of these iodinated phenyl carbonate compounds provides an effective method for various X-ray and other applications while also eliminating the additional step of withdrawing or otherwise physically eliminating the bolus of placed radiopaque from the cavity after the particular application is completed, such removing steps being common to prior art methods in this area. This embodiment further provides a method for accomplishing the desired application without providing irritation to the body cavity or other undesirable side effects or problems with administering the radiopaque also common to prior art methods.

One object of the present invention is thus to provide a new and improved method for visualizing an inner body cavity which eliminates many problems of administration and undesirable side effects while also eliminating the need for physical removal of the radiographic agent from the body cavity after the application is completed.

Other objects and advantages of the present invention will become apparent as the following description proceeds.

DESCRIPTION OF THE PREFERRED EMBODIMENT

For the purposes of explaining and promoting a better understanding of the present invention, and the preferred method thereof, the following description and disclosure will be divided into three parts, as follows: First, disclosure will be made of the iodinated phenyl carbonate compounds comprising one embodiment of the present invention. Second, disclosure will be made of the preferred method of the invention, as previously discussed. Third, specific examples will be given of the preparation of such compounds and their use in this preferred method.

According to the present invention, it has been found that iodinated phenyl carbonates, and particularly p-iodo-benzyl carbonates, p-iodo-sec-phenethyl carbonates, p-iodo-phenethyl carbonates, p-iodo-phenyl carbonates, 3-acetamido-(2,4,6-triiodobenzyl)ethyl carbonates, p-iodobenzyl ethyl carbonates, 3-(p-iodophenyl)propyl carbonates, 3-(p-iodophenyl)butyl carbonates, 2-(p-iodobenzyl)butyl carbonates and 2-(p-iodobenzyl)-n-hexyl carbonates, have many unexpected and valuable properties when used as radiographic media in connection with such current techniques as X-ray applications including myelography, salpingography, lymphography and bronchography. These compounds may be characterized generally as carbonates having the general formula:

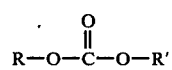

wherein R represents an alkyl group having from 1 to 10 carbon atoms and R' represents iodinated phenyl linked directly to the ester oxygen or through an alkyl chain (which may be a lower alkylene chain) consisting of 1 to 3 carbon atoms. These compounds may be further limited into a subclass characterized by the following general formula:

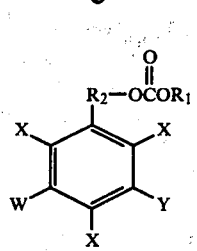

wherein $R_1$ is a lower alkyl group consisting of straight or branched chains having from 1 to 10 carbon atoms, wherein $R_2$ is a lower alkylene chain linking the aromatic ring to the carbonate by 0 to 3 carbon atoms and has attached thereto a constituent selected from the group including hydrogen and alkyl groups with 1 to 4 carbon atoms, X is selected from the group including hydrogen and iodine (1 to 3 iodine), and W and Y are each selected from the group including hydrogen, iodine, amine and acetamido with at least W or Y being iodine when X is hydrogen.

In accordance with the present invention, it has been discovered that certain iodinated phenyl carbonates exhibit many unexpected and valuable properties when used as radiopaques or radiographic media. Such iodinated phenyl carbonates find particular but not necessarily exclusive utility as radiographic media for use in X-ray applications including myelograpy, salpingography, lymphography and bronchography.

In a preferred form, the aromatic ring is substituted primarily by one iodine atom in the para position. Table I shows a number of compounds of the foregoing type which are useful in accordance with the present invention.

Table I-continued

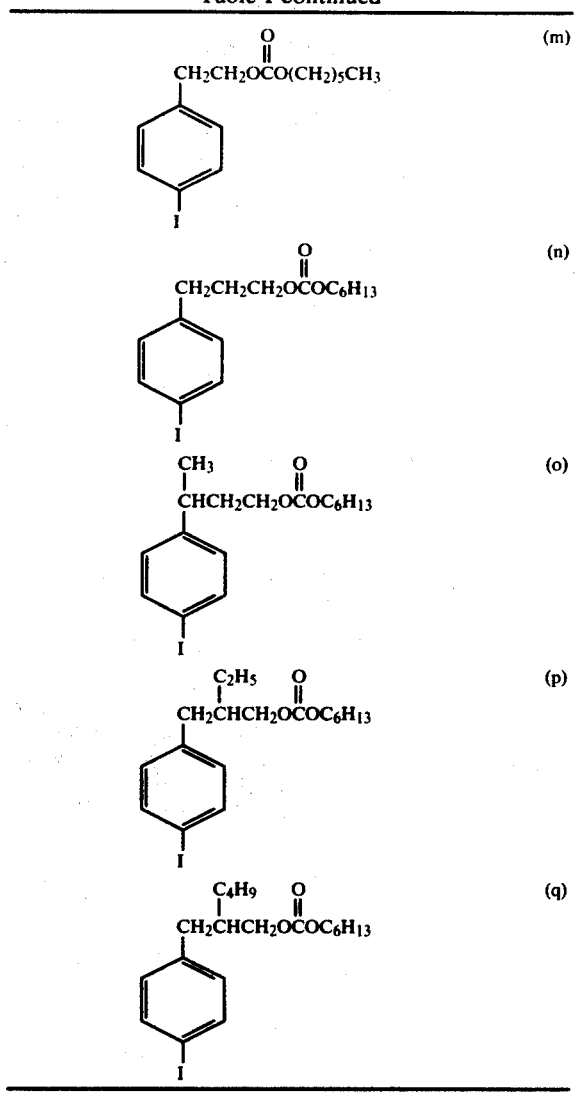

The aromatic ring may also be substituted by an iodine in the meta and/or ortho positions or by more than one iodine or by both iodine and an amine. Examples of such compounds are:

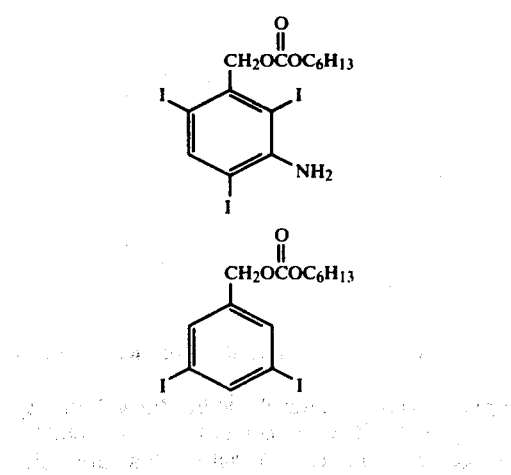

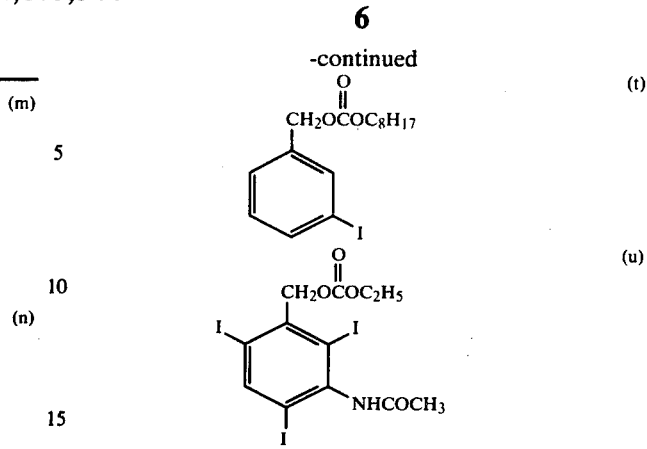

A prior art example of substitution of an aromatic ring by a carbon atom with the carbonate having the general formula as set forth hereinabove and including R with a single carbon atom is shown by the formula

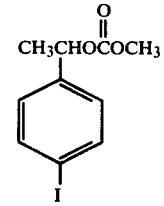

As an initial toxicity screen for the compounds shown hereinabove, the neat liquid or suspension of the material was injected into the peritoneal cavity of albino mice and the Approximate Lethal Dose (ALD) determined using the method of Deichmann and LeBlanc (W. B. Deichmann and T. J. LeBlanc, *J. Ind. Hyg.*, 25, 415 (1943)) the results of which are presented in Table II, as set forth hereinafter.

As can be seen from Table II compound v of the prior art is more toxic and hence this structure with its single carbon atom has been considered not suitable for uses contemplated for this invention. However, when the phenyl structure contains an acetamido group, or a similar radical which assists in detoxifying the compound while also possibly increasing its solubility, the compound becomes pharmaceutically acceptable for uses contemplated for this invention. For example, see the ALD result in Table II for 3-acetamido-(2,4,6-triiodobenzyl) ethyl carbonate which has only 2 carbon atoms trailing the carbonate radical, but which also has an acetamido radical at the 3-, or Y, position.

Previous to this invention, the carbonate linkage was not an obvious moiety for radiographic use. However, with the success realized with the compounds as set forth in Table I, it follows that the carbonate linkage can be incorporated into still other compounds with particular extensions thereof being listed as follows:

Table II

Approximate Interperitoneal Toxicity in Mice

| Compound No.[a] | Approximate Lethal Dose Ml/Kg |
|---|---|
| a | 3 |
| b | 3 |
| c | 7 |
| d | 7 |
| e | 15[b] |
| f | 10.5[b] |
| g | 15 |

Table II-continued

Approximate Interperitoneal Toxicity in Mice

| Compound No.[a] | Approximate Lethal Dose Ml/Kg |
|---|---|
| h | 3 |
| i | 15[b] |
| j | 7 |
| k | 7 |
| l | 10.5 |
| m | 7 |
| n | 15 |
| o | 7 |
| p | greater than 15[b] |
| q | greater than 15[b] |
| r | greater than 11[b] [c] |
| s | 5 |
| t | greater than 17 |
| u | greater than 22[c] |
| v | 1.5 |

[a]See designated formulas hereinabove for structures.
[b]This was the largest dose adminstered.
[c]20% w/v in Sesame oil, no deaths seen with neat Sesame oil.

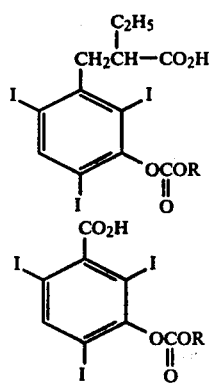

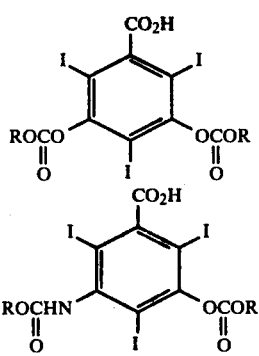

-continued

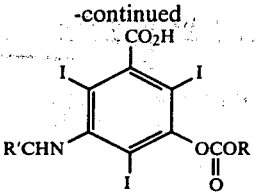

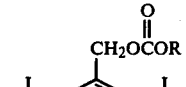

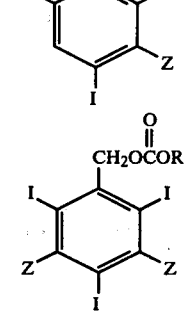

wherein, R has the meaning as indicated above and Z is an amine, lower alkanol or acetamido or another detoxifying radical.

Many of these iodinated phenyl carbonates may be synthesized by one of the following general procedures, referring to p-iodobenzyl carbonate as a representative example:

Procedure A

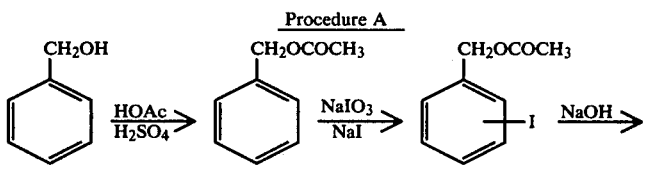

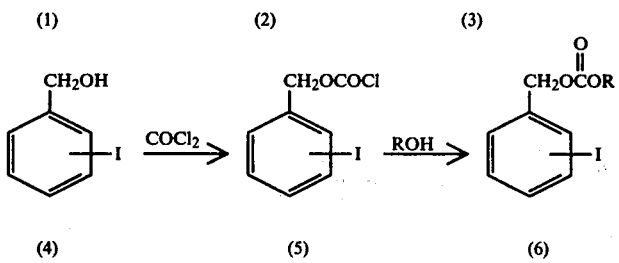

Procedure B

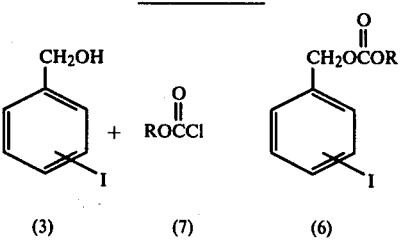

For preparation of the preferred forms, R is as described above.

The iodination procedures depicted above for many of the compounds described herein require the combination of glacial acetic acid, concentrated sulfuric acid, iodine and sodium iodate. Under these conditions alcohols are converted to acetate esters. For example, in Procedure A treatment of benzyl alcohol (1) with glacial acetic acid and concentrated sulfuric acid forms the acetate ester (2). The simultaneous presence of iodine and sodium iodate gives iodobenzyl acetate (3) in one step. This ester is not isolated but is hydrolized with base to give easily isolated iodobenzyl alcohol (4). The iodinated alcohol is converted to the chloroformate (5) by treatment with phosgene. Conversion of the chloroformate to the desired carbonate (6) is then achieved by addition of the desired alochol, ROH. For those compounds of Formula I where $R_2$ is sec-phenethyl, the acetate ester is prepared by treating sec-phenethyl alcohol with glacial acetic acid and p-toluene sulfonic acid. The isolated ester is then iodinated by the procedure outlined above. The conversion of the iodinated acetate to the alcohol and the preparation of the carbonates remains the same.

When the alkyl chloroformate (7) is available, many of the compounds of Formula I can be prepared by Procedure B. That is, the alkyl chloroformate (7) in a suitable solvent (e.g. chloroform) is added to the iodinated alcohol (3), thus forming the desired carbonate (6).

In the preferred method of the present invention, iodinated phenyl carbonate compounds, such as those described above, are used in a method for visualizing an inner body cavity in a human being or other animal. Accordingly, the first step of this preferred method is the selecting of a pharmaceutically acceptable iodinated phenyl carbonate compound. A "pharmaceutically acceptable" compound, as used herein, means a compound which is sufficiently nontoxic to be used and which exhibits the trait of being eliminated by the normal body processs as further discussed hereinbelow. Examples of acceptable compounds within this classification are the specific iodinated phenyl carbonates described and depicted hereinabove.

The second step of this preferred method is the placing of an amount of selected iodinated phenyl carbonate material into the subject body cavity under examination. In this regard, "amount" and "effective amount" are meant to define a quantity in cubic centimeters, or otherwise, of the selected compound providing sufficient, or effective, radiographic contrast to permit successful examination of the particular body cavity. Obviously, this "effective amount" of the carbonate compound will vary significantly according to the particular cavity under review. The "effective amount" will also vary according to the animal to be examined, it being clear that examination of a human being will require the use of substantially greater amounts than will examination of corresponding cavities in laboratory dogs or mice. These "effective amounts" are known in the art and are obtainable from existing records and procedures. Accordingly, the specific quantity or amount placed into a cavity has little importance to the preferred method so long as it is sufficient to provide the necessary contrast for the particular X-ray or other application.

The same is true with the specific manner, or way, in which the placing is accomplished. Known procedures are available for the various X-ray and other applications contemplated within the scope of the present invention. Whether the placing is accomplished by injection through a hollow needle, insufflation or surgical incision and direct application is of little significance to the preferred method of the present invention. And regardless of the specific procedure employed, it is often desirable to bring the iodinated phenyl carbonate to about body temperature prior to the placing and then to place the compound into the cavity while at about the body temperature.

Upon this placing, the quantity of iodinated phenyl carbonate compound will form into a bolus in the cavity thereby establishing the radiopaque contrasting background to permit X-ray or other examination of the cavity itself. The exact position of the bolus within the cavity at any point of time can be determined by standard fluoroscopy procedures in preparation for the X-ray examination.

The final active step in the preferred method is then the X-raying of this body cavity and the performing, or conducting, of a particular radiographic study of the cavity. This final step can be accomplished using standard procedures known in the art for the particular application under study. In this regard, more than one X-ray is often taken of the cavity under study, sometimes from different angles or positions in order to obtain a more complete picture of the condition of the subject area. These X-rays are also often taken over an extended period of time as the bolus of iodinated phenyl carbonate moves and flows through the cavity thereby providing a complete visualization of the subject cavity. This "extended period" can be from 30 minutes to about 1 day or even longer depending, of course, upon the initial size of the placed bolus, the specific compound used and its viscosity, and the relative size of the cavity itself.

When the X-ray study is complete, the visualization process is ended and the preferred method of the present invention accomplished. Noticeably absent from this preferred method is any final surgical or other step designed to physically remove the radiopaque material from the body cavity after examination. For this reason, the preferred method and iodinated phenyl carbonates of the present invention constitute significant improvements over established prior art methods and radiopaques. Specifically, testing to date has shown the rates of degradation and absorption for these iodinated phenyl carbonates are significantly higher than for existing prior art compounds, with absorption and elimination by the normal body processes being accomplished within a period of less than about six weeks depending, once again, upon the initial size of the placed bolus, the specific compound used and its viscosity, and the relative size and location of the subject cavity.

Therefore, the final passive step of the preferred method of the present invention is merely to allow the placed iodinated phenyl carbonate compound to be absorbed and eliminated by these normal body processes. In this regard, the term "normal body processes" is meant to include those bodily systems normally involved in handling waste disposal such as, for example, the lympographic system and the blood system.

The following examples are now given as further illustrations of the preferred embodiments of the present invention and should not be considered in any way as limitations or restraints on the embodiments as discussed herein and defined in the attached claims. With this one caveat, examples of the preparation of several iodinated phenyl carbonate compounds and of specific methods for their use as radiographic contrast agents according to the present invention are as follows. In

EXAMPLE 1 p-Iodobenzyl Alcohol

A solution of glacial acetic acid (1350 ml.) and iodine (250 g.) was heated to 100° and then concentrated sulfuric acid (140 ml. of 95–97%) added, followed by benzyl alcohol (216 g.). Sodium iodate (92 g.) in water (500 ml.) was then introduced dropwise with stirring over a period of 1 hour. The temperature was maintained at 100°–110° for an additional 30 minutes before the reaction mixture was poured onto 1 Kg. of crushed ice. The mixture was extracted with chloroform, the combined chloroform solution washed with water, dried, and concentrated. The remaining oil was distilled at reduced pressure to give p-iodobenzyl alcohol. A mass spectrum (70 ev) parent ion was measured at m/e 233.9545; calculated for $C_7H_7IO$, 233.9544. The ir and nmr spectrum were in agreement with the proposed structure. The use of a mass spectrum for identification of compounds is shown, for example, in R. Venkataraghaven, R. D. Broad, R. Klimowsky, J. W. Amy, and F. W. McLafferty, *Adv. Mass Spec.*, 4, 65 (1967) and R. Venkataraghaven, R. J. Klimowsky, F. W. McLafferty, *Acc. Chem. Res.*, 3, 158 (1970).

EXAMPLE 2 p-Iodobenzyl Chloroformate

A three-necked flask was fitted with a gas delivery tube and an exit tube connected to a calcium chloride drying tube. A stirring bar was added. The third neck of the flask was stoppered and the delivery and exit tubes fitted with pinch cocks so that the reaction vessel could be disconnected for weighing. Toluene (100 ml.) was introduced into the flask and the vessel weighed. After cooling to 0° in an ice/salt bath, phosgene was bubbled through the toluene until a weight gain of 30 g. was obtained. p-Iodobenzyl alcohol, (46.2 g.) as prepared in Example 1, in toluene (100 ml.) was then added rapidly. After stirring at 0° and then at room temperature the solution was concentrated by distillation under reduced pressure at a temperature not exceeding 60°. The solution of p-iodo-benzyl chloroformate was stoppered and stored until needed.

EXAMPLE 3 p-Iodobenzyl Carbonates

A three-necked flask was fitted with a thermometer, a drying tube and a dropping funnel containing the p-iodobenzyl chloroformate (0.2 moles) solution prepared as described in Example 2, to which chloroform (300 ml.) had been added. An alcohol (0.8 moles), of the type ROH as described above in Procedure A, was introduced in the flask along with 320 ml. of pyridine and a stirring bar. After cooling to about 0°, the chloroformate solution was added dropwise to the flask while maintaining the temperature below 5°. After adding the chloroformate solution, the reaction mixture was warmed to room temperature and stirred for 1 hour. The reaction mixture and 800 ml. of 6 N HCl were added simultaneously with stirring to 400 ml. of 3 N HCl in 800 g. of crushed ice. The resulting aqueous phase was extracted with chloroform (3×100 ml.). All chloroform phases were combined and backwashed with water (2×100 ml.). The chloroform solution was dried with anhydrous magnesium sulfate and concentrated under reduced pressure. Finally, the pure carbonate was obtained by distilling the oil at reduced pressure.

EXAMPLE 4

The carbonate synthesis Procedure B was used for this Example. A three-necked flask fitted with a thermometer and an addition funnel was arranged for magnetic stirring. p-Iodobenzyl alcohol (0.3 moles) from Example 1 was dissolved in chloroform (300 ml.) and the solution transferred to the reaction vessel along with pyridine (61 ml.). After cooling in an ice/salt bath, a solution of the desired alkyl chloroformate

(ROCCl in Procedure B)

10% excess, in chloroform (175 ml.) was added dropwise while maintaining the temperature below 5°. After completing the addition, the reaction mixture was heated to 50° and held there for 30 min. The reaction mixture was poured into 1 liter of water and extracted with chloroform. The combined chloroform solution was back-washed with water and dried. After removing the chloroform on a rotary evaporator, the oil was distilled at reduced pressures giving the desired carbonate.

EXAMPLE 5 p-Iodobenzyl Isobutyl Carbonate (a of Table I)

The carbonate synthesis of Procedure A was used for this preparation. p-Iodobenzyl chloroformate, in chloroform, was added to a solution of 2-methyl-1-propanol in pyridine. The carbonate was isolated as a colorless oil and had a refractive index of $N_D^{25}=1.5421$. A mass spectrum (70 ev) parent ion was measured at m/e 334.0064, and calculated for $C_{12}H_{15}IO_3$ at 334.0068. An ir and nmr were in agreement with the proposed structure.

EXAMPLE 6 n-Amyl-p-Iodobenzyl Carbonate (b of Table I)

The carbonate synthesis of Procedure A was used for this preparation. p-Iodobenzyl chloroformate in chloroform was added to a solution of n-amyl alcohol in pyridine. The isolated n-amyl-p-iodobenzyl carbonate was a colorless oil with a refractive index of $N_D^{25}=1.5439$. A mass spectrum (70 ev) parent ion was measured at m/e 348.0231, and calculated for $C_{13}H_{17}IO_3$ at 348.0225. An ir and nmr were in agreement with the proposed structure.

EXAMPLE 7 n-Hexyl-p-Iodobenzyl Carbonate (c of Table I)

The carbonate synthesis of Procedure A was used for this preparation. p-Iodobenzyl chloroformate in chloroform was added to a solution of n-hexanol in pyridine. Colorless n-hexyl-p-iodobenzyl carbonate was isolated by distillation and had a refractive index of $N_D^{25}=1.5368$. A mass spectrum (70 ev) parent ion was measured at m/e 362.0362, and calculated for $C_{14}H_{19}IO_3$ at 362.0381. An ir and nmr were in agreement with the proposed structure.

EXAMPLE 8 p-Iodobenzyl-4-methyl-2-Pentyl Carbonate (d of Table I)

This compound was prepared using the carbonate synthesis of Procedure A. p-Iodobenzyl chloroformate was added to a pyridine solution of 2-methyl-4-pentanol. The recovered carbonate was a colorless oil having a refractive index of $N_D^{25} = 1.5320$. A mass spectrum (70 ev) parent ion was measured at m/e 362.0373, and calculated for $C_{14}H_{23}IO_3$ at 362.0381. An ir and nmr were in agreement with the proposed structure.

EXAMPLE 9 n-Octyl-p-Iodobenzyl Carbonate (e of Table I)

The carbonate synthesis of Procedure A was used for this preparation. p-Iodobenzyl chloroformate was added to a solution of n-octyl alcohol in pyridine. Vacuum distillation gave n-octyl-p-iodobenzyl carbonate with a refractive index of $N_D^{25} = 1.5299$. A mass spectrum (70 ev) parent ion was measured at m/e 390.0673, and calculated for $C_{16}H_{23}IO_3$ at 390.0694. An ir and nmr were in agreement with the proposed structure.

EXAMPLE 10 n-Decyl-p-Iodobenzyl Carbonate (f of Table I)

This preparation was carried out using the carbonate synthesis of Procedure A. After adding p-iodobenzyl chloroformate to a pyridine solution of n-octyl alcohol at 0°, the desired n-dectyl-p-iodobenzyl carbonate was isolated by vacuum distillation. The colorless, viscous oil had a refractive index of $N_D^{25} = 1.5224$. A mass spectrum (70 ev) parent ion was measured at m/e 418.1002, and calculated for $C_{18}H_{27}IO_3$ at 418.1007. An ir and nmr were in agreement with the proposed structure.

EXAMPLE 11

2-Ethylhexyl-p-Iodobenzyl Carbonate (g of Table I)

The carbonate synthesis of Procedure A was used for this preparation. p-Iodobenzyl chloroformate, in chloroform, was added to a solution of 2-ethyl hexanol in pyridine. The recovered material was vacuum distilled, giving colorless oil with a refractive index of $N_D^{25} = 1.5295$. A mass spectrum (70 ev) parent ion was measured at m/e 390.0661, and calculated for $C_{16}H_{23}IO_3$ at 390.0694. The ir and nmr spectra were in agreement with the proposed structure.

EXAMPLE 12

2-Octyl-p-Iodobenzyl Carbonate (i of Table I)

This compound was prepared from p-iodobenzyl alcohol and 2-octyl alcohol using the carbonate synthesis of Procedure A. Vacuum distillation of the recovered material gave a colorless oil having a refractive index of $N_D^{25} = 1.5259$. A mass spectrum (70 ev) parent ion was measured at m/e 390.0665, and calculated for $C_{16}H_{23}IO_3$ at 390.0694. The ir and nmr spectra were in agreement with the proposed structure.

EXAMPLE 13

3-Hexyl-p-Iodobenzyl Carbonate (h of Table I)

p-Iodobenzyl alcohol and 3-hexanol were reacted as outlined in the carbonate synthesis of Procedure A. The recovered material was distilled to give 3-hexyl-p-iodobenzyl carbonate. The refractive index was $N_D^{25} = 1.5248$. A mass spectrum (70 ev) parent ion was measured at m/e 362.0359, and calculated for $C_{14}H_{19}IO_3$ at 362.0384. The ir and nmr spectra were in agreement with the proposed structure.

EXAMPLE 14 n-Hexyl-p-Iodophenyl Carbonate (j of Table 1)

p-Iodophenol reacted with n-hexylchloroformate according to the carbonate synthesis of Procedure B. n-Hexyl-p-iodophenyl carbonate was isolated from the recovered material by vacuum distillation. The compound gave a refractive index of $N_D^{25} = 1.5340$. A mass spectrum (70 ev) parent ion was measured at m/e 348.0210, and calculated for $C_{13}H_{17}IO_3$ at 348.0225. The nmr and ir spectra were in agreement with the proposed structure.

EXAMPLE 15 n-Octyl-p-Iodphenyl Carbonate (k of Table I)

The combination of p-iodophenol with n-octylchloroformate, by means of the carbonate synthesis of Procedure B, gave a crude material containing the desired carbonate. Vacuum distillation successfully separated the carbonate from the starting materials. The colorless oil had a refractive index of $N_D^{25} = 1.5244$. A mass spectrum (70 ev) parent ion was measured at m/e 376.0548, and calculated for $C_{15}H_{21}IO_3$ at 376.0538. The ir and nmr spectra were in agreement with the proposed structure.

EXAMPLE 16 sec-Phenethyl Acetate

A three-necked, round-bottom flask was fitted with a mechanical stirrer and a jacketed tube heated with steam. The top of the steam-heated tube was vented to a water-cooled condenser, and the apparatus arranged so that the upper phase of the condensate would return to the round-bottom flask. The flask was charged with 1.4 moles sec-phenethyl alcohol, 120 ml. glacial acetic acid, 250 ml. benzene, and 1.4 grams p-toluene sulfonic acid. After refluxing the reaction mixture for 7 hours, the mixture was extracted with 10% aqueous sodium bicarbonate and water. The benzene solution was then dried with magnesium sulfate and the benzene removed by evaporation. The crude sec-phenethyl acetate was iodinated and hydrolyzed using the procedure outlined above for p-iodobenzyl alcohol. Distillation of the recovered material at reduced pressure gave the desired p-iodo-sec-phenethyl alcohol. The isolated material had a refractive index of $N_D^{25} = 1.6046$. A mass spectrum (70 ev) parent ion was measured at m/e 247.9680, and calculated for $C_{18}H_8IO$ at 247.9700. The ir and nmr spectra were in agreement with the proposed structure.

EXAMPLE 17 n-Hexyl-p-Iodo-sec-Phenethyl Carbonate p-Iodo-sec-phenethyl alcohol was treated with n-hexylchloroformate as outlined in the carbonate synthesis of Procedure B. The recovered products were distilled at reduced pressure to give the desired carbonate. The ir and nmr spectra of the oil were in complete agreement with the proposed structure. The refractive index was $N_D^{25} = 1.5265$. A mass spectrum (70 ev) parent ion was measured at m/e 376.0531, and calculated for $C_{15}H_{21}IO_3$ at 376.0538.

EXAMPLE 18 p-Iodophenethyl Alcohol

Phenethyl acetate was converted to p-iodophenethyl alcohol using the procedure outlined for the preparation of p-iodobenzyl alcohol. The isolated material had a refractive index of $N_D^{25} = 1.6155$. The mass spectrum (70 ev) parent ion was measured at m/e 247.9685, and calculated for $C_8H_9IO$ at 247.9700. The ir and nmr spectra were in agreement with the proposed structure.

EXAMPLE 19 n-Hexyl-p-Iodophenethyl Carbonate (m of Table I)

p-Iodophenethyl alcohol was reacted with n-hexylchlorofromate according to the carbonate synthesis of Procedure B. The isolated material gave an ir and nmr spectra in agreement with the proposed structure. The oil had a refractive index of $N_D^{25} = 1.5295$. The mass spectrum (70 ev) parent ion was measured at m/e 376.0508, and calculated for $C_{15}H_{21}IO_3$ at 376.0538.

Analysis: (1) calculated $C_{15}H_{21}IO_3$: C, 47.91; H, 5.63; and (2) found: C, 48.07; H, 5.66.

EXAMPLE 20 n-Hexyl-3-(p-Iodophenyl)Propyl Carbonate
Preparation of n in Table I:

(a) 3-Phenyl Propyl Acetate

Using the procedure outlined in Example 16, 3-phenylpropanol was converted to 3-phenyl propyl acetate.

(b) 3-(p-Iodophenyl)Propanol

Using the procedure outlined in Example 1, 3-phenyl propyl acetate was converted to 3-(p-iodophenyl)propanol ($N_D^{25} = 1.6048$).

(c) n-Hexyl-3-(p-Iodophenyl)Propyl Carbonate

Using the procedure outlined in Example 4, 3-(p-iodophenyl)propanol was treated with n-hexyl chloroformate giving n in Table I ($N_D^{25} = 1.5291$).

Mass spectrum (70 ev) parent ion was measured at 390.0708, and calculated for $C_{16}H_{23}IO_3$ at 390.0694.

EXAMPLE 21 n-Hexyl-3-(p-Iodophenyl)Butyl Carbonate

Preparation of o in Table I:

(a) 3-Phenyl Butanol

A reaction vessel was fitted with a mechanical stirrer, thermometer and a reflux condenser capped with an additional funnel. While under a positive flow of dry nitrogen, the system was flame dried. The vessel was charged with 250 ml. of benzene; and then 25 g. of aluminum chloride was added as quickly as possible. This mixture was cooled with stirring to 5° C. in an ice/salt bath and a solution of 7.2 g. (0.1 mol) of crotyl alcohol in 45 ml. of benzene was added dropwise while maintaining the temperature below 5° C. Next, 50 ml. of concentrated hydrochloric acid was added cautiously. After warming to room temperature, 50 ml. of water was added and the lower organic phase removed. The aqueous portion was then extracted with benzene. The combined organics were washed with aqueous 10% sodium bicarbonate and water. After drying over anhydrous magnesium sulfate, filtering and evaporating, a dark oil was recovered. This was vacuum distilled to give 8.2 g. of colorless 3-phenyl butanol ($N_D^{25} = 1.5210$).

(b) 3-(p-Iodophenyl)Butanol

Using the procedure outlined in Example 1, 3-phenylbutanol was converted to 3-(p-iodophenyl)butanol. Mass spectrum (70 ev) parent ion was measured at 275.9993, and calculated for $C_{10}H_{13}IO$ at 276.0013.

(c) n-Hexyl-3-(p-Iodophenyl)Butyl Carbonate

Using the procedure outlined in Example 4, 3-(p-iodophenyl)butanol was treated with n-hexyl chloroformate giving o in Table I $N_D^{25} = 1.5289$. Mass spectrum (70 ev) parent ion was measured at 404.0830, and calculated for $C_{17}H_{25}IO_3$ at 404.0850.

EXAMPLE 22 n-Hexyl-2-(p-Iodobenzyl)Butyl Carbonate

Preparation of p in Table I:

(a) α-Ethyl Cinnamic Acid

Benzaldehyde was condensed with potassium butyrate and butyric anhydride according to the procedure as outlined in the patent to Archer, U.S. Pat. No. 2,931,830 to give α-ethyl cinnamic acid, with a m.p. at 104°–104.8° C.

(b) 2-Benzyl Butanoic Acid

A solution of 35.2 gm (0.2 mol) of α-ethyl cinnamic acid in 450 ml. of 3% sodium hydroxide was reduced in a hydrogen atmosphere at 60 psi using 4 g. of 5% palladium on charcoal. After hydrogen uptake had ceased, the reaction mixture was filtered, acidified with hydrochloric acid and extracted with ether. Evaporation gave 36 g. (0.2 mol) of 2-benzyl butanoic acid.

(c) 2-Benzyl Ethyl Butanoate

A flame dried round-bottom flask was fitted with a condenser capped with a calcium chloride drying tube. A solution of 8.8 g. (0.05 mol) of 2-benzyl butanoic acid and 25 ml. of thionyl chloride was refluxed overnight. The excess thionyl chloride was removed at 14 mm of Hg under under dry conditions. Next a solution of 20 ml. of absolute ethanol in 30 ml. of benzene was added and the reaction refluxed for 16 hours. The reaction was then evaporated to an oil, 200 ml. water added and this extracted with ether. After drying over magnesium sulfate, the ether was removed yielding 10 gm of 2-benzyl ethyl butanoate as a red-brown oil.

(d) 2-Benzyl Butanol

A three-necked, round-bottom flask was fitted with a mechanical stirrer, addition funnel and reflux condenser. After flame drying the system, 11.7 g. (0.3 mol) of lithium aluminum hydride in 125 ml. of anhydrous ester was added and the mixture heated to reflux. The heat was removed and a solution of 38 g. (0.18 mol) of 2-benzyl ethyl butanoate in 75 ml. of anhydrous ether was added dropwise at such a rate that refluxing was maintained. The reaction was heated at reflux for an additional 30 minutes and then 45 ml. of ethyl acetate added with caution. Next, 135 ml. of 6 N hydrochloric acid was added, followed by 225 ml. of water. The reaction mixture was extracted with ether, the ether dried over anhydrous magnesium sulfate and evaporated to give 29.6 g. (0.17 mol) of crude 2-benzyl butanol.

(e) 2-(p-Iodobenzyl)Butanol

Using the procedure outlined in Example 1, 2-benzyl butanol was converted to 2-(p-iodobenzyl)butanol ($N_D^{25} = 1.5886$). Mass spectrum (70 ev) parent ion was measured at 290.0141, and calculated for $C_{11}H_{15}IO$ at 290.0169.

(f) Hexyl-2-(p-Iodobenzyl)Butyl Carbonate

Using the procedure outlined in Example 4, 2-(p-iodobenzyl)butanol was treated with n-hexyl chloroformate to give p in Table I ($N_D^{25}=1.5250$).

Mass spectrum (70 ev) parent ion was measured at 418.0994, calculated for $C_{18}H_{27}IO_3$ 418.1007.

EXAMPLE 23 n-Hexyl-2-(p-Iodobenzyl)-n-Hexyl Carbonate

Preparation of q in Table I:
(a) 2-(p-Iodobenzyl)Hexanol

Using the procedure outlined for the preparation of 2-(p-iodobenzyl)butanol, but conducting the initial condensation with benzaldehyde, potassium hexanoate and hexanoic anhydride, 2-(p-iodobenzyl)hexanol was recovered ($N_D^{25}=1.5446$). Mass spectrum (70 ev) parent ion was measured at 318.0470, and calculated for $C_{13}H_{19}IO$ at 318.0482.

(b) n-Hexyl-2-(p-Iodobenzyl)-n-Hexyl Carbonate

Using the procedure outlined in Example 4, 2-(p-iodobenzyl)hexanol was treated with n-hexyl chloroformate giving q in Table I ($N_D^{25}=1.5250$).

Mass spectrum (70 ev) parent ion was measured at 446.1320, and calculated for $C_{20}H_{31}IO_3$ at 446.1320.

EXAMPLE 24

3-Amino-2,4,6-Triiodobenzyl-n-Hexyl Carbonate

Preparation of r in Table I:

Using the procedure outlined in Example 4, 3-amino-2,4,6-triiodobenzyl alcohol, prepared according to the procedure set forth by J. Hebky and M. Karasek in *Coll. Czech. Chem. Commun.*, 29, 3103 (1964), was treated with n-hexyl chloroformate. The recovered crude material was dissolved in hot hexane/benzene and after cooling, the solid removed. Evaporation of the mother liquor gave a solid which on recrystallization from ethanol/water gave r in Table I (m.p. of 89.6°–90.6°).

Analysis: (1) calculated for $C_{14}H_{18}I_3NO_3$: C, 26.72; H, 2.88; and (2) found: C, 26.70; H, 3.19.

EXAMPLE 25

3,5-Diiodobenzyl-n-Hexyl Carbonate

Preparation of s in Table I:

Using the procedure of B, Gaux and D. LeHenaff, *Bull. Soc. Chem. Fr.*, 34, 505 (1974), 2,3,5-triiodobenzoic acid (Aldrich) was treated with lithium aluminum hydride to give 3,5-diiodobenzyl alcohol with m.p. of 136.5°–140° (literature 137°). Using the procedure outlined in Example 4, 3,5-diiodobenzyl alcohol was treated with n-hexyl chloroformate giving s in Table I ($N_D^{25}=1.5800$).

Analysis: (1) calculated for $C_{14}H_{18}I_2O_3$: C, 34.43; H, 3.72; I, 52.02; and (2) found: C, 34.69; H, 3.90, I, 51.81.

EXAMPLE 26 m-Iodobenzyl-n-Octyl Carbonate

Preparation of t in Table I:

Using the procedure outlined in Example 4, m-iodobenzyl alcohol (Aldrich) was treated with n-octyl chloroformate giving t in Table I ($N_D^{25}=1.5232$).

EXAMPLE 27 p-Iodo-sec-Phenethyl Methyl Carbonate

Preparation of v in Table I:
Using the procedure outlined in Example 4, p-iodo-sec-phenethyl alcohol was treated with methyl chloroformate giving v in Table I ($N_D^{25}=1.5584$; R. Taylor, *J. Chem. Soc.* (B) 622 (1971), with $N_D^{25}=1.5611$).

EXAMPLES 28–33

Lymphographic Study of Laboratory Animals

Four iodinated organic carbonates prepared as described hereinabove were evaluated for use as lymphographic agents in laboratory dogs. The selected compounds were p-iodobenzyl ethyl carbonate, p-iodobenzyl-n-hexyl carbonate, p-iodobenzyl-n-butyl carbonate and p-iodobenzyl-n-octyl carbonate. Also one iodinated organic thiolcarbonate, S-(p-iodobenzyl)-n-butyl thiolcarbonate, was evaluated. The compounds were compared with the performance of Ethiodol, a known prior art radiopaque for such applications, in a sixth dog for effective lymph duct filling, radiographic quality, elimination rate and histopathological effects.

Six adult mongrel dogs, preconditioned for at least two weeks at the Lafayette Pharmacal, Inc. facilities, were used for the study. The dogs were removed from food the evening prior to dosing. Each animal was first anesthetized with Rompun and sodium pentobarbital and intubated to assist in breathing. A standard lymphogram was then performed on one rear leg only of each animal using known laboratory procedures. Specifically, a blue dye was first injected between the toes of the right hind limb to locate the lymph ducts. A single duct was then disected out and cannulated. One of the six compounds was then selected and a syringe pump used to inject the test compound into the duct at a constant rate. In this regard, the dogs were injected with an effective amount of one (1) cc of test substance per 20 lbs. of body weight. The iodinated phenyl compounds were brought to about body temperature prior to the injecting and then were injected while at about the body temperature.

Radiographs were then taken of each animal after confirming the location of the injected bolus by fluoroscopy means. The animals were given atropine sulfate and observations made while they were allowed to recover from the anesthetic unassisted.

The animals were then returned to their cages and radiographs were taken at the end of 24 hours, 3 days and 1, 2, 3, 4 and 6 weeks to determine the radiographic clearance rate of each tested compound. Daily urine samples were also collected and subjected to fluorescent exitation analysis to determine the urinary clearance rate for each compound. Six weeks after the initial lymphogram, the animals were sacrificed and the popliteal and iliac nodes on both sides removed. The nodes from the dosed side and undosed side of each animal were then compared histopathologically.

The following observations and conclusions were made: All of the test animals responded well to the procedure with all test materials being well tolerated. At no time during the observation period following lymphography were any clinical signs of side effects demonstrated as a result of the compounds. The nodes of the dog dosed with p-iodobenzyl ethyl carbonate were cleared in approximately three (3) days by the normal body processes. The rate of clearance and elimination of the radiographic agents then increased from fastest to slowest as follows: p-iodobenzyl ethyl carbonate, S-(p-iodobenzyl)-n-butyl thiolcarbonate, p-iodobenzyl-n-butyl carbonate, p-iodobenzyl-n-hexyl carbonate, p-iodobenzyl-n-octyl carbonate and ethiodol. The rate of clearance for S-(p-iodobenzyl)-n-butyl thiolcarbonate and p-iodobenzyl-n-butyl carbonate were almost the same.

Dogs dosed with p-iodobenzyl-n-butyl carbonate, S-(p-iodobenzyl)-n-butyl thiolcarbonate and p-iodobenzyl-n-hexyl carbonate were radiographically clear in six (6) weeks or less. The popliteal node in the dog dosed with p-iodobenzyl-n-octyl carbonate was clear at six (6) weeks but small droplets could be seen in the iliac node. In contrast, the nodes in the dog dosed with ethiodol were clearly visible radiographically after six (6) weeks.

Half-lives were tabulated from the fluorescent exitation analysis of the urine samples from the examined dogs. The half-lives were as follows for the five tested iodinated compounds, corresponding to their order of rate of clearance as indicated above: 0.36 days; 1.08 days, 1.73 days; 1.39 days; and 1.58 days. The half-life for ethiodol, because of its slow elimination rate, could not be calculated.

Histopathology of the nodes of each animal was very encouraging in that all five of the tested iodinated phenyl carbonate compounds performed superior to, i.e., causing less histopathological response, the ethiodol compound. Specifically p-iodobenzyl-n-butyl carbonate and p-iodobenzyl ethyl carbonate produced no change in the nodes dosed with the test materials. S-(p-iodobenzyl)-n-butyl thiolcarbonate and p-iodobenzyl-n-octyl carbonate gave responses histopathologically in the dosed nodes of mild granulomatous lymphadenitis or lipoidal lymphadenopathy. p-Iodobenzyl-n-hexyl carbonate and Ethiodol evidenced more severe reactions with moderate lipoidal lymphadenitis. p-Iodobenzyl-n-hexyl carbonate also gave granulomatous lymphadenitis accompanied by casious necrosis.

In summary, p-iodobenzyl ethyl carbonate and p-iodobenzyl-n-butyl carbonate were indistinguishable from undosed animals after six weeks. S-(p-iodobenzyl)-n-butyl thiolcarbonate and p-iodobenzyl-n-octyl carbonate also gave excellent overall results with only minor histopathological responses after six weeks. All of these compounds responded better than ethiodol.

EXAMPLES 34–41

Suboccipital Study of Laboratory Animals

Six iodinated phenyl carbonate compounds prepared as described above, as well as air and Pantopaque, a known prior art radiographic compound, were injected suboccipitally into separate groups of 30 laboratory rats. The six iodinated compounds under examination were p-iodobenzyl-n-hexyl carbonate, p-iodobenzyl-n-octyl carbonate, p-iodobenzyl-2-octyl carbonate, 2-ethylhexyl-p-iodobenzyl carbonate, n-hexyl-3-(p-iodophenyl)propyl carbonate and n-hexyl-2-(p-iodobenzyl)-butyl carbonate. Six rats from each injected group were then sacrificed at periodic intervals and the brain and spinal cord removed for histopathological evaluation. By comparing the results of air and Pantopaque with the results using the iodinated compounds, an evaluation of their relative neurotoxicity was obtained.

The groups of rats were first subjected to standard quarantine procedure at the Lafayette Pharmacol, Inc. facilities for at least two weeks prior to dosing. About 18 hours prior to dosing, food was withdrawn but water was allowed ad lib. During injection, each animal was anesthetized in an ether chamber and the back of the neck closely clipped. After placing the animal on a board with the head declined at 45°, a puncture was made just at the base of the atlas and 0.1 ml. of the selected test substance was injected. Radiographs were then taken immediately after dosing to confirm the intrathecal location of the injected bolus, and the animals were returned to their cages for observation.

One group of six animals for each tested substance was then sacrificed at the following elapsed times post injection: 1 week; 2 weeks; 4 weeks; 8 weeks and 14 weeks. At sacrifice, the animal were perfused with saline and formalin. Each animal was again radiographed and the brain and spinal cord then removed and stored for histopathological study.

In general, the animals responded well to the injection of the test substances. Air and Pantopaque produced minimal responses in the test animals. p-Iodobenzyl-n-octyl carbonate and n-hexyl-2-(p-iodobenzyl)butyl carbonate produced overall responses close to air and Pantopaque approximating normal, but with slightly more lipid puddle formation and with an occasional animal showing some difficulty with righting responses. Relatively more severe histopathological responses were recorded for 2-ethylhexyl-p-iodobenzyl carbonate, p-iodobenzyl-2-octyl carbonate, n-hexyl-3-(p-iodophenyl)propyl carbonate and p-iodobenzyl-n-hexyl carbonate, with more animals exhibiting righting difficulty and as a group taking longer to recover from the injection procedure. All of the animals in the study appeared normal before the 8-week sacrifice date.

EXAMPLES 42–48

Bronchography Study of Laboratory Animals

Five healthy dogs housed at the Lafayette Pharmacal, Inc. facilities for a year or more were selected for bronchographic examination using 3-acetamido-(2,4,6-triiodobenzyl)ethyl carbonate (compound u depicted hereinabove). Food was withdrawn from each animal 12 hours prior to dosing with water given ad lib. The animals were then first anesthetized with sodium pentobarbital and maintained on halothane. Each animal was then intubated with a tracheal tube and scouting X-ray films were taken to confirm its position. Next, a stainless steel guide wire was passed through a polypropylene tube, i.e., insulation tube, and this combination was passed into the animal's lung. The position of this guide wire was then confirmed by fluoroscopy and the guide wire then removed, thus leaving the insulation tube in place.

Next, a DeVilbiss powder blower preweighed with an amount of 3-acetamido-(2,4,6-triiodobenzyl)ethyl carbonate was connected to the insulation tube. In this regard, the amount of selected iodinated phenyl carbonate compound varied for each animal according to weight, with 6 cc being given to the heaviest test dog. Oxygen at 20 psi was then used to insuflate a caudal lobe of one lung of each animal while monitoring with fluoroscopy. Lateral and direct view radiographs were then taken. The insuflation tube was removed and the powder blower weighed to obtain a better estimation of the amount of compound insuflated into the animal's lung. When each animal showed signs of recovery from the anesthetic, the endotracheal tube was withdrawn and the animal returned to its cage. Food was then given after 12 hours.

Although one animal exhibited occasional coughing the morning following the injection procedure, all of the animals were without signs of difficulty after 2 days. At 2 weeks, the animals were then anesthetized and radiographs taken while the lungs were expanded by air insuflation. The animals were then sacrificed by injection of saline and the dosed lobe of each animal examined histopathologically and compared with the corresponding undosed lobe.

No gross lesions were found that appeared specifically related to instillation of the contrast medium. Some lobes were collapsed on both treated and control sides of the lungs and probably were related to manipulations at the time of instillation of the compound. Certain histopathological alterations, however, were produced by the intrapulmonic instillation procedure. These lesions, not found in control lobes, consisted of an obliterative granulomatous bronchiolitis. The small bronchioles were generally filled, so the lumen was obliterated, by a granulomatous response consisting of histiocytes, epitheloid cells and in some foci by foreign body giant cells.

There was some evidence the iodinated phenyl carbonate had persisted and was responsible for this granulomatous bronchiolitis. This evidence consisted of small cystic spaces or slits containing fibrillar or amorphous grannular material within the granulomas. Atelectasis and emphysema occurred in both control and treated portions of the lungs of the test animals and were either agonal changes relating to the death of the dogs or to handling of the tissues themselves. The tracheitis condition existing in several animals was most probably related to mild trauma produced by tracheal intubation and not by the 3-acetamido-(2,4,6-triiodobenzyl)ethyl carbonate material.

What is claimed is:

1. A method for visualizing an inner body cavity in an animal comprising:
   (a) placing an effective amount of a pharmaceutically acceptable iodinated phenyl carbonate compound into a body cavity in an animal; and
   (b) X-raying the body cavity.

2. The method of claim 1 wherein the pharmaceutically acceptable iodinated phenyl carbonate compound is of the formula

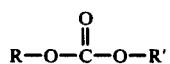

wherein:
   (a) R is a lower alkyl group consisting of a straight or branched chain having from 1 to 10 carbon atoms; and
   (b) R' is an iodinated phenyl linked directly to the ester oxygen or through a lower alkylene group consisting of a straight or branched chain having from 1 to 3 carbon atoms.

3. The method of claim 2 wherein the pharmaceutically acceptable iodinated phenyl carbonate compound is of the formula

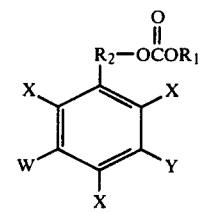

wherein:
   (a) $R_1$ is a lower alkyl group consisting of a straight or branched chain having from 1 to 10 carbon atoms;
   (b) $R_2$ is a lower alkylene chain linking the aromatic ring to the carbonate by 0 to 3 carbon atoms and having attached thereto a constituent selected from the group consisting of hydrogen and alkyl groups with 1 to 4 carbon atoms;
   (c) X is selected from the group consisting of hydrogen and iodine; and
   (d) W and Y are each selected from the group consisting of hydrogen, iodine, amine and acetamido when X is iodine, at least W or Y being iodine when X is hydrogen.

4. The method of claim 3 wherein the iodinated phenyl carbonate compound is capable of elimination by the normal body processes within less than about six weeks following said placing.

5. The method of claim 3 wherein said X-raying comprises performing a radiographic study of the body cavity, said performing including X-raying the cavity from different angles and over a period of time as the placed amount of iodinated phenyl carbonate moves inside the cavity in order to obtain visualization of the complete inner body cavity.

6. The method of claim 1 additionally comprising the step of allowing the placed amount of iodinated phenyl carbonate to be eliminated by the normal body processes.

7. The method of claim 1 wherein said placing comprises injecting through a needle.

8. The method of claim 1 wherein said placing comprises insuflating through a tube.

9. The method of claim 7 which additionally includes bringing the iodinated phenyl carbonate to about body temperature prior to said injecting and injecting said compound while at about the body temperature.

* * * * *